United States Patent [19]

Mehl

[11] Patent Number: 4,733,671
[45] Date of Patent: Mar. 29, 1988

[54] TISSUE NEEDLE

[76] Inventor: Donald N. Mehl, 3794 Williston Rd., Minnetonka, Minn. 55343

[21] Appl. No.: 26,889

[22] Filed: Mar. 17, 1987

[51] Int. Cl.⁴ .............................................. A61B 10/00
[52] U.S. Cl. .................................... 128/754; 128/310
[58] Field of Search ................ 128/749, 751, 754, 310

[56] References Cited

U.S. PATENT DOCUMENTS 4,282,884  8/1981  Boebel .................................. 128/754
4,667,684  5/1987  Leigh .................................... 128/754

FOREIGN PATENT DOCUMENTS 1178422  9/1985  U.S.S.R. ............................. 128/754

Primary Examiner—Kyle L. Howell
Assistant Examiner—Randy Citrin
Attorney, Agent, or Firm—Hugh D. Jaeger

[57] ABSTRACT

Tissue needle for extracting a biopsy sample including a pistol style squeezable hand grip for single hand biopsy tissue needle operation. A spring tensioned sliding cannula, including a configured cutting edge, actuates by a squeeze trigger and cam arrangement to slide over a fixed position stylet for entry into a tissue sample area. A squeeze trigger manually cycles using one hand to obtain a biopsy sample contained in a tissue sample notch of the sharp stylet tip whereupon the tissue needle is manually withdrawn. The soft tissue can be liver tissue, kidney tissue, growth area tissue, or a like tissue. The tissue needle can have other medical biopsy uses in either human or animals.

3 Claims, 17 Drawing Figures

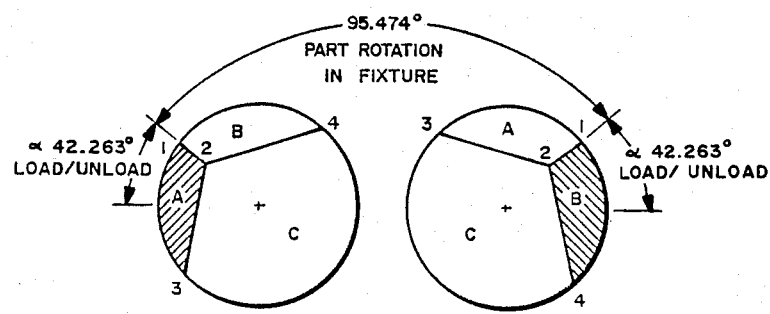
FIG. 13C POSITION "X" END VIEW
POSITION "Y" REF. FIG. 13D 4,733,671

TISSUE NEEDLE

BACKGROUND OF THE INVENTION

1. Field of the Invention

The present invention relates to a tissue sampling device, and more importantly, pertains to a single hand operation biopsy tissue needle.

2. Description of the Prior Art

Prior art biopsy needles features needles whereby a cannula and stylet were both operated using different actuating members. Once the needle was inserted, extreme care had to be taken to insure that the proper actuator member be moved in the proper sequence so that the needle members would not access the wrong tissue area or move inadvertently past or out of the desired biopsy tissue area, causing irritation or puncturing of an undesired tissue area. Often the user practitioner, due to unfamiliarity with the needle or procedure, would operate the needle members in an opposite and undesired direction, causing undue stress and trauma in, at or about adjacent tissue areas. Very detailed operational instructions were often hard to follow and required practice on the part of the practitioner, sometimes at the expense of a patient. Another problem was that in having two operating members, two hands were required for proper action of the prior are tissue needles when obtaining a biopsy sample.

The present invention overcomes the disadvantages of the prior art by providing a tissue needle requiring single-handed operation at the biopsy point.

SUMMARY OF THE INVENTION

The general purpose of the present invention is a single handed manually operated biopsy needle.

According to one embodiment of the present invention, there is provided a piston grip tissue needle wherein a sliding cannula, including a configured sliding edge, positions co-axially to slide over a fixed position stylet. A squeeze trigger actuates a linkage arm to cause a linkage block and the attached cannula to slide over the stylet to cut a biopsy sample contained in a tissue sample notch. A return spring returns the cannula to an unactuated position when pressure upon the squeeze trigger is released.

One significant aspect and feature of the tissue needle, the present invention, is a needle requiring physical actuation of a single member to obtain a core tissue sample.

Another significant aspect and feature of the present invention is a fixed position needle sharp stylet positioned in a gripping handle and a cannula for sliding thereover.

Another significant aspect and feature of the present invention is a spring biased return cannula.

Another significant aspect and feature of the present invention is a tissue needle requiring only one hand for proper operation.

Yet another significant aspect and feature of the present invention is a cannula actuated by a linkage arm connected to a squeeze trigger actuator bar arrangement.

Another significant aspect and feature of the tissue needle is a handle contoured to a user's hand.

Having thus described the principal embodiments of the present invention, it is a principal object hereof to provide a tissue needle.

One of the objects of the present invention is to provide a tissue needle operable by one hand whereby only a simple squeezing action is required.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designated like parts throughout the figures thereof and wherein.

DESCRIPTION OF THE PREFERRED EMBODIMENT

Figure 1:
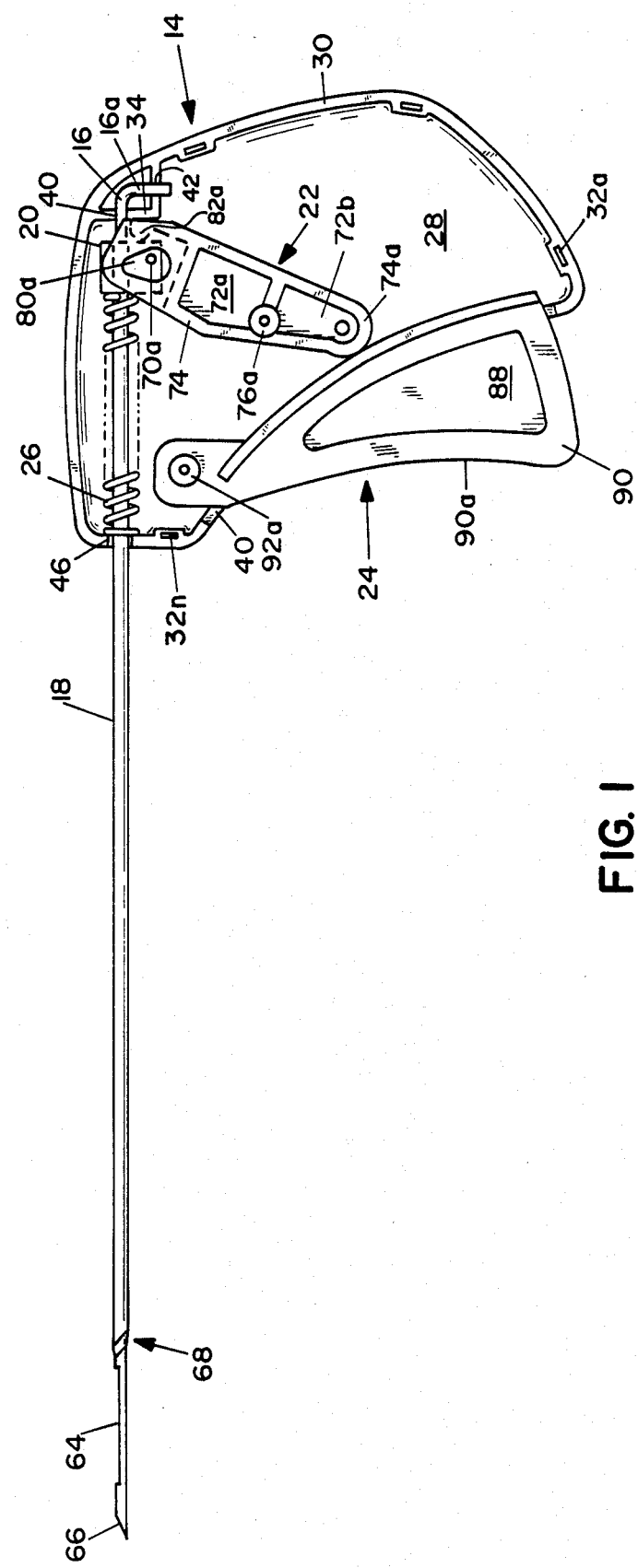
FIG. 1 illustrates a side elevation of a tissue needle, the present invention.

FIG. 1 illustrates a side elevation view of a tissue needle 10, the present invention, where a cover half is removed for purposes of illustration. The tissue needle 10 includes handle half members 12 and 14, a stationary stylet 16, a sliding cannula 18 mounted coaxially to stationary stylet 16, a linkage block 20, a linkage arm 22, a trigger or actuator bar 24 and a compression spring 26 mounted over and about the cannula 18 where all elements position in or affix to configured handle member 14 as illustrated in the figure. Configured handle member 14, also illustrated in FIG. 3, includes side member 28, raised edge member 30, alignment slots $32a$–$32n$ adjacent to and inwardly from the raised edge member 30, and a raised right angle member 34 affixed to and of corresponding height to the affixed raised edge member 30, and including half holes 40 and 42 aligned perpendicularly to each other in the upper surface $34a$ of right angle member 34. A raised cylindrical actuator bar pivot member 36 projects inwardly from side member 28 and includes a pivot hole $36a$, a raised cylindrical linkage arm pivot member 38 projecting inwardly from side member 28 and including a pivot hole $38a$, and an actuator bar cutout 44 for accommodation of the actuator bar 24. A half hole 46, slightly larger than the cannula 18, positions in the upper left portion of raised edge member 30 for sliding accommodation of the sliding cannula 18. The like and opposite mirror like image handle half 12, as also illustrated in FIG. 4, positions over and about handle half 14 and the elements contained therein. The handle half 14 includes a side member 48, a riased edge 50, alignment tabs 52a–52n adjacent to and projecting outwardly from the raised edge 50 for engagement with alignment slots 32a–32n in the handle half 14. A right angle member 54 corresponding to the right angle member 34 in the handle half 14 secures the portions of the stylet adjacent to the bend 16a of the stylet 16 in the half holes 40 and 42 of the handle half 14 by the juxtaposition of the upper surface 54a against and over the surface 34a, thus securing the portions of the stylet 16 positioned within the half holes 40 and 42. A raised cylindrical actuator bar pivot member 56 projects inwardly from the side member 48 includes a pivot holes 56a. A raised cylindrical linkage arm pivot member 58 projects inwardly from the side member 48 and includes pivot hole 58a. A sliding cannula accommodation hole 60, slightly larger than the cannula 18, and actuator bar cutout 62 which corresponds to like elements 44 and 46 in the handle half 14 position in the raised edge 50 of the handle half 12. The fixed position stylet 16 positions interiorally and co-axially within a cylindrical cavity 63 of the sliding cannula 18 and also passes through a hole 100 in the linkage block 20, as described in FIGS. 10 and 11. A flat ground tissue sample notch 64 positioned longitudinally in close proximity to a compound cut tip 66 described later in detail in the figures. The cannula 18 and the linkage block 20 slide laterally along the stylet 16 and against the compression spring 26. The opposite end of the spring 26 positions against the raised edge 30 and 50 in the area of the half holes 46 and 60. One end of the cannula 18 positions in and is secured within the linkage block 20 as described later in detail in FIGS. 9, 10, and 11. The other end of the cannula 18 near the compound cut tip 66 includes a tissue cutting tip 68 as later described in detail in FIG. 9. Capture pins 70a and 70b the positioned on the lower portion of the vertical sides 20a and 20b of the linkage block 20 to assure the alignment of linkage block 20 and the sliding cannula 18, and provides secure attachment of the block 20 to the linkage arm 22.

Figure 5:
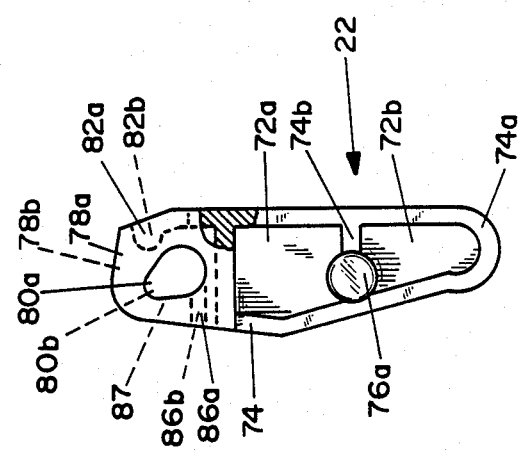
FIG. 5 illustrates a side view of the linkage arm.
Figure 6:
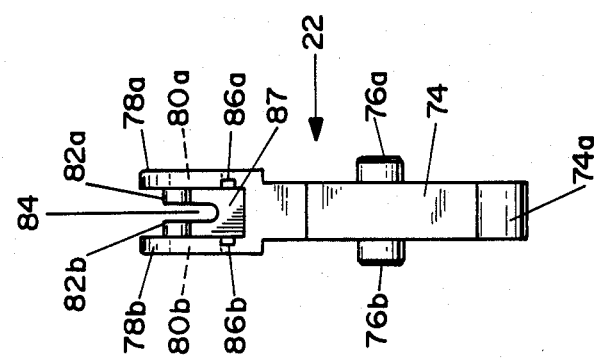
FIG. 6 illustrates an end view of the linkage arm.
Figure 10:
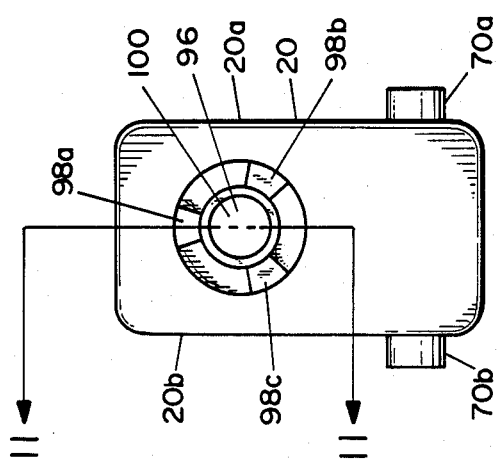
FIG. 10 illustrates an end view of the linkage block.

Configured linkage arm 22, also illustrated in FIGS. 5 and 6, includes planar midsections 72a and 72b, a raised edge 74, a rounded raised edge portion 74a, a raised edge 74b dividing the planar midsection 72a and 72b, cylindrical pivot points 76a and 76b and upper opposed mirror image planar sides 78a and 78b. As illustrated in FIGS. 5 and 6, dual radius cam holes 80a and 80b position as illustrated in the planar sides 78a and 78b to accommodate the actuating pins 70a and 70b of the linkage block 20 as illustrated in FIG. 10. Linkage block actuator cams 82a and 82b and a slot 84 disposed therebetween position between the sides 78a and 78b as illustrated in FIGS. 5 and 6. Slot 84 accommodates the stylet 16 during the operational mode of the tissue needle 10. Small position slots 86a and 86b illustrated in FIGS. 5 and 6 position interiorly to the sides 78a and 78b for accommodation of the actuating pins 70a and 70b during product assembly. Cavity 87 shown in FIGS. 5 and 6 positions interiorly to the sides 78a and 78b to accommodate the linkage block 20. Cylindrical pivot points 76a and 76b position in the pivot members 38 and 58 of the handle halves 14 and 12, respectively. The actuator bar 24 contacts the rounded raised portion 74a of the linkage arm 22 to cause rotational movement of the linkage arm 22 in a counterclock-wise fashion about pivot points 76a and 76b and actuation of the sliding cannula 18 along the stylet 16. The configured arced actuator bar 24 includes an inner planar member 88, an outer planar member 90, thicker and heavier with respect to the inner planar member 88, and includes an arced finger grip surface or manual actuating surface 90a which conforms to the inwardly arced cutout portions 44 and 62 of the handle halves 14 and 12. Pivot point members 92a and 92b oppose each other on the upper faces 90c and 90d of the planar member 90, and position in the cylindrical pivot members 56 and 36. A radiused or arced linkage arm actuator member 94 positions perpendicularly to the planar member 90, and is essentially a substantially rectangular member which conforms to the curvature of the planar member 90.

MODE OF OPERATION

Figure 2:
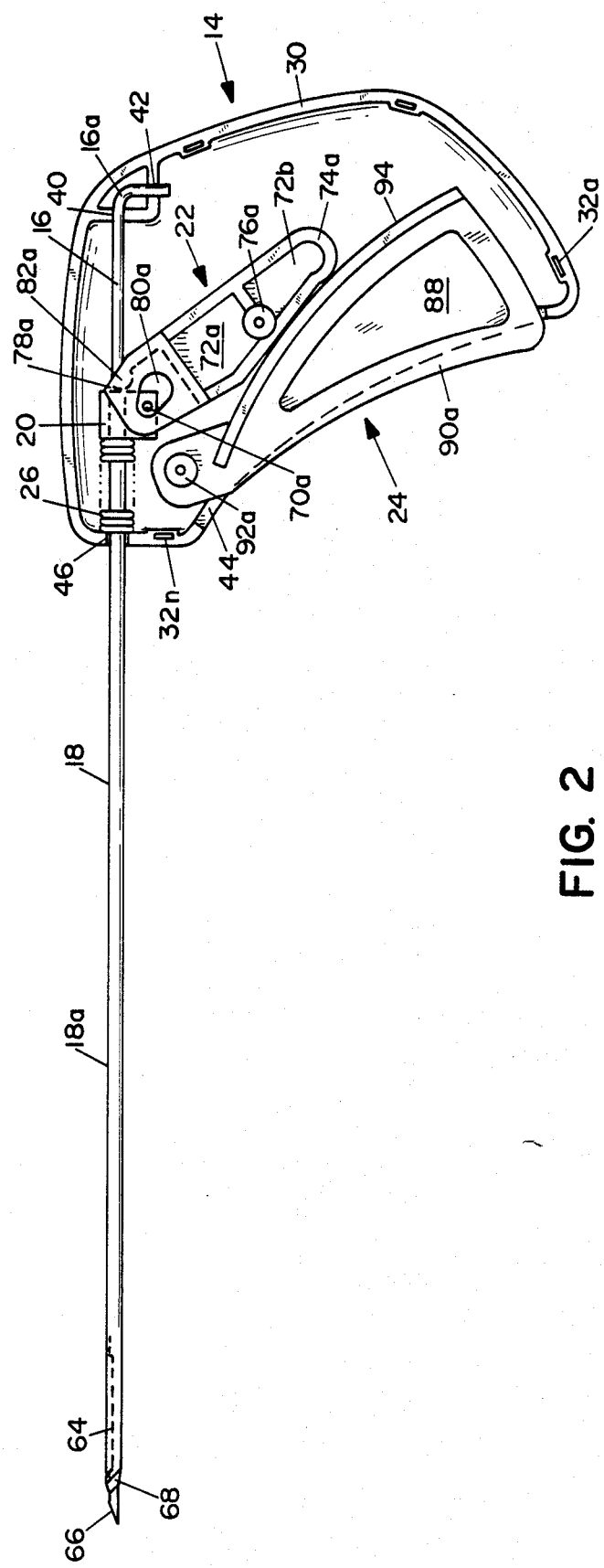
FIG. 2 illustrates a side elevation of a tissue needle in an operational mode.

FIG. 2 illustrates a side elevation of the tissue needle 10, and the mode of operation where all numerals correspond to those elements previously decribed. Prior to entry of the tissue needle 10 into the biopsy area, the actuator bar 24 is squeezed manually by the physician. The arced actuator member 94 contacts against the rounded raised edge portion 74a causing the linkage arm 22 to rotate in a counter-clockwise fashion to slide the linkage block 20 and the sliding cannula 18 laterally along the stylet 16. Upon full depression of the actuator bar 24, the tissue bias-cut cutting tip 68 of the sliding cannula encompasses and fully encloses the tissue sample notch 64 within the confines of the cylindrical walls of the cannula 18 as illustrated. The bias-cut cannula cutting tip 68 positions adjacent to the stylet tip 66 to form a streamlined low profile point for entry into the biopsy area.

The physician now holds the tissue needle 10 with one hand, and causes through force the stylet 16 and cannula 18 to enter the biopsy tissue area. After entry to the tissue area, the actuating bar 24 is released while holding the handles 12 and 14 in the same relative position to the tissue. The cannula 18 returns by action of the compression spring 26 against the linkage block 20 and retracts the cannula fully inwardly to the position illustrated in FIG. 1, exposing the tissue sample notch 64 whereupon tissue sample enters the sample notch 64. The physician then depresses the actuator bar 24 to cause the sliding cannula 18 and the biased-cut cutting tip 68 to traverse the stylet 16, and cut a plug like tissue sample that is captured within the same notch and within the portion of the cannula wall 18a that overlies the sample notch 64. Then with the tissue sample contained in the sample notch 64 and all elements positioned as in FIG. 2, the tissue needle 10 is withdrawn from the area the tissue sample is taken from. Upon removal, the actuator bar 24 is released and the sliding cannula 18 is retracted exposing the sample tissue contained in the tissue sample notch 64 so that the tissue sample may be removed from the tissue needle 10 for laboratory analysis.

It is noted that only one hand is required for complete operation of the tissue needle 10 itself, leaving the physicians other hand free to provide support or external manipulation as needed about the biopsy area as required.

Figure 3:
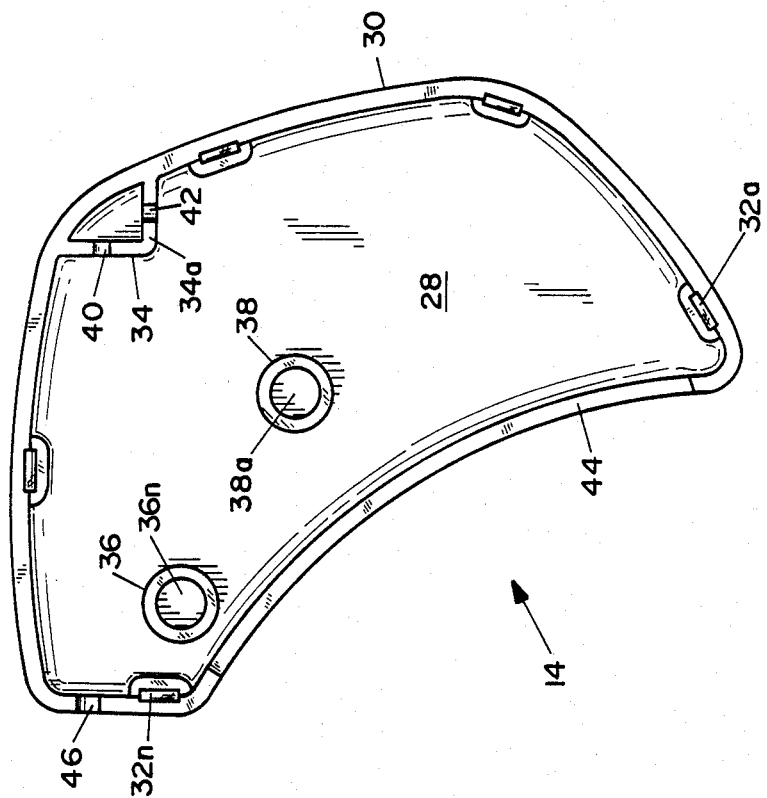
FIGS. 3 and 4 illustrate a side elevation of opposing handle interiors of the tissue needle.
Figure 4:
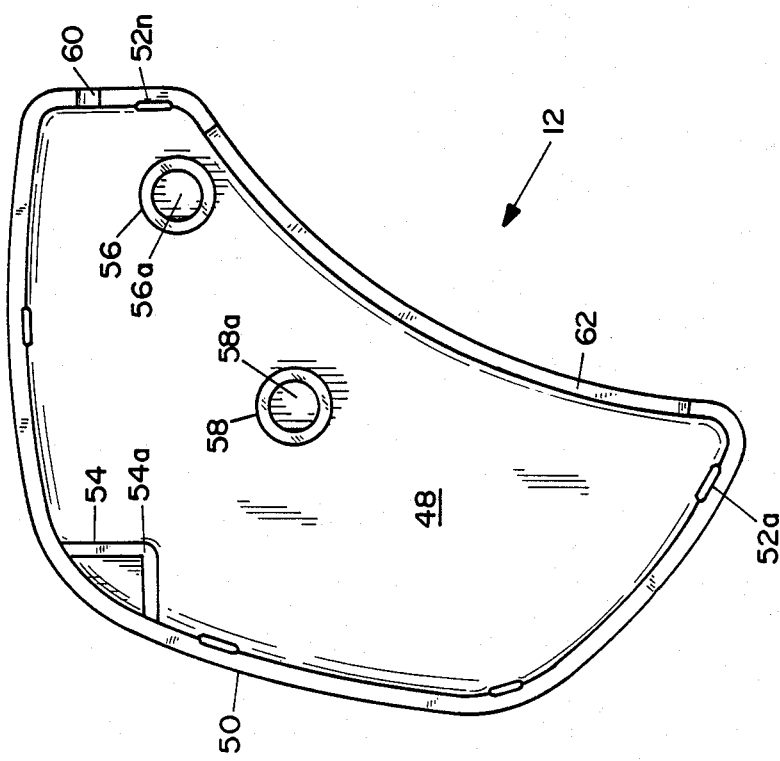

FIG. 3 illustrates a side elevation of the right tissue needle handle 14 where all numerals correspond to those elements previously described. Shown in particular are the sliding cannula accommodation hole 46, the perpendicularly aligned stylet capturing holes 40 and 42, and the cylindrical pivotal members 36 and 38. The exterior surfaces of both halves can be textured to provide a superior gripping surface on each side of the handles.

FIG. 4 illustrates a side elevation of the left tissue needle handle 12 where all numerals correspond to those elements previously described. Shown in particular in this illustration are members corresponding to the right handle including the sliding cannula accommodation hole 60, the cylindrical pivotal members 56 and 58, and the alignment pins 52a-52n which align with slots 32a-32n of handle half 14 of FIG. 3.

FIG. 5 illustrates a side view of the linkage arm 22 where all numerals correspond to those elements previously described. Shown in particular is the orientation of the cam holes 80a-80b which allow proper capture of the pins 70a-70b when the holes 80a-80b move in an arc during actuation of the linkage arm 22.

FIG. 6 illustrates an end view of the linkage arm 22 where all numerals correspond to those elements previously described. The cavity 87 is shown between the sides 78a and 78b for accommodation of the linkage block 20. The slot 84 between the linkage block actuator cams 82a and 82b accommodates the stylet 16 as the linkage arm travels in an arcular path during cannula actuation.

Figure 7:
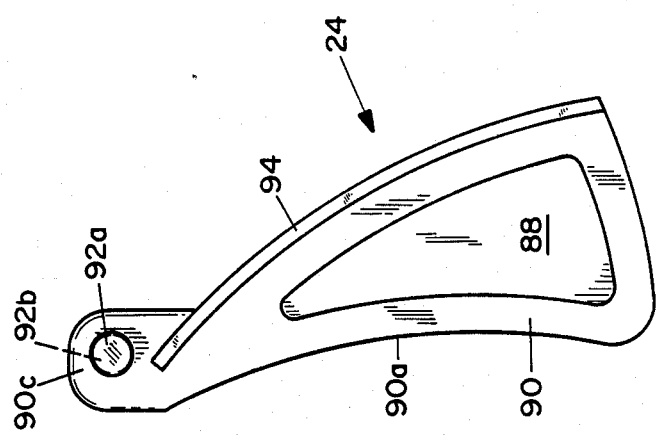
FIG. 7 illustrates a side view of the actuator bar.

FIG. 7 illustrates a side view of the actuator bar 24 where all numerals correspond to those elements previously described.

Figure 8:
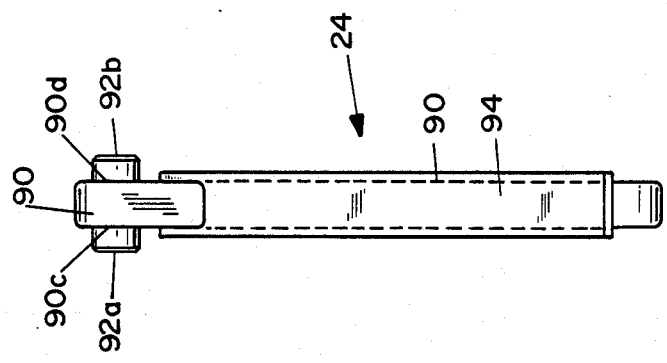
FIG. 8 illustrates an end view of the actuator bar.

FIG. 8 illustrates an end view of the actuator bar 24 where all numerals correspond to those elements previously described. Shown in particular are the pivot point members 92a and 92b positioned on the opposing faces 90c and 90d of the configured planar member 90.

Figure 9:
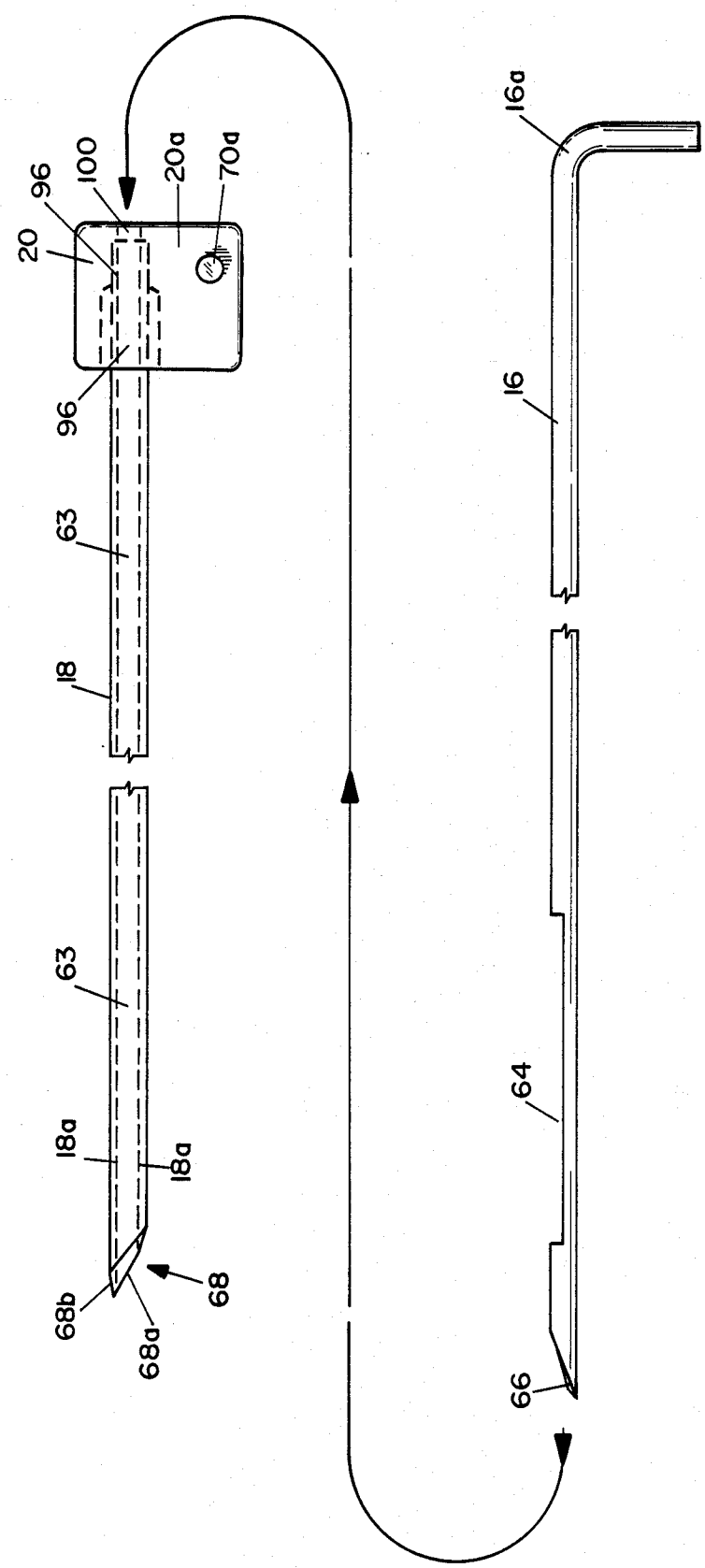
FIG. 9 illustrates a side view of the stylet and cannula.
Figure 11:
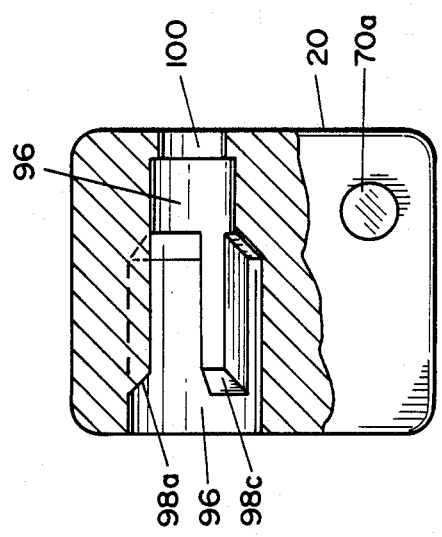
FIG. 11 illustrates a cutaway side view of the linkage block taken along line 11—11 of FIG. 10.

FIG. 9 illustrates a side view of the linkage block 20, the stylet 16, and the cannula 18 where all numerals correspond to those elements previously described. An end of the cannula 18 is cemented or otherwise likely secured in the dual radiused hole 96 in the linkage block 20. Ribs 98a, 98b and 98c, as illustrated in FIGS. 10 and 11, position about the larger inner circumference of the dual radiused hole 96 to position and support the end of the cannula 18 in the dual radiused hole 96. A bonding agent is applied between the ribs 98a-98c to secure the cannula 18 within the dual radiused hole 96. Another hole 100 in the linkage block 20 aligns with the hole 96 to permit entry of stylet 16 into the hole 63 in the center of cannula 18. The angled cutting tip 68 is cut on a bias 68b to effect the ellipsoid cutting edge 68a. Biasing of the tissue cutting tip 68 allows for streamlined entry into the tissue sample area as described in FIG. 2.

FIG. 10 illustrates an end view of the linkage block 20 where all numerals correspond to those elements previously described. The ribs 98a-98c are shown positioned radially about the large diameter of the dual radiused hole 96.

FIG. 11 illustrates a partial cross section taken along line 11—11 of FIG. 10 where all numerals correspond to those elements previously described. The ribs 98a and 98c are illustrated positioned in the dual radius hole 96.

Figure 12:
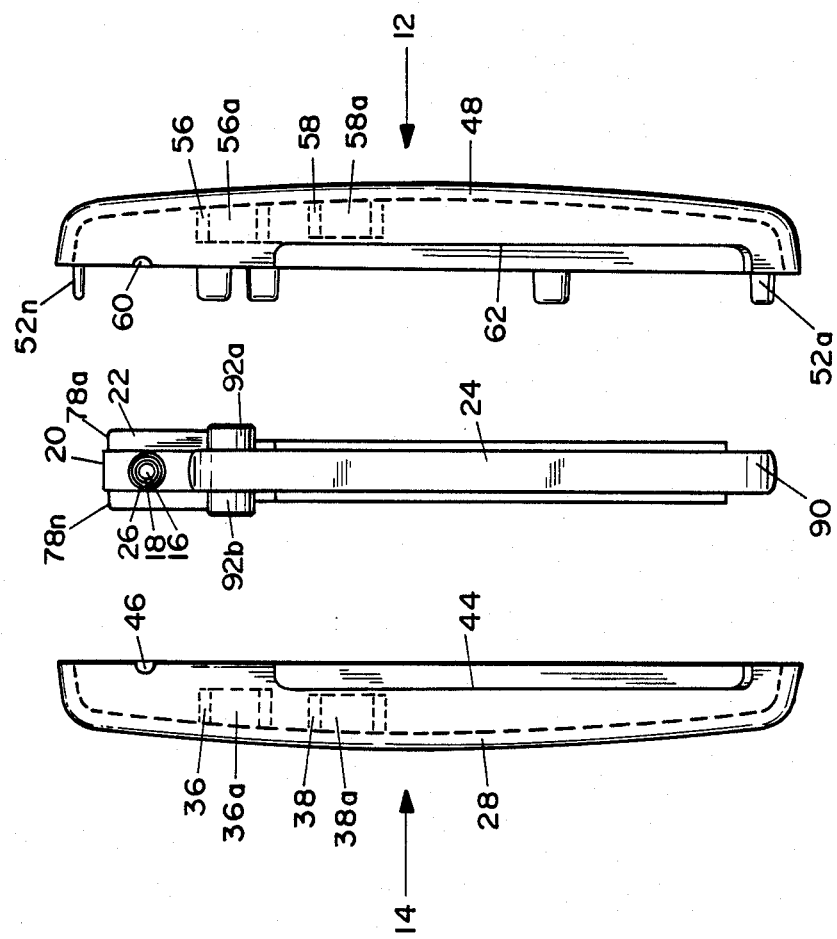
FIG. 12 illustrates an exploded end view of the handles about the actuator bar and linkage arm prior to assembly.

FIG. 12 illustrates as exploded end view of the handle halves 12 and 14, the linkage block 20, the linkage arm 22 and the actuator bar 24 prior to assembly where all numerals correspond to those elements previously described.

Figure 13A:
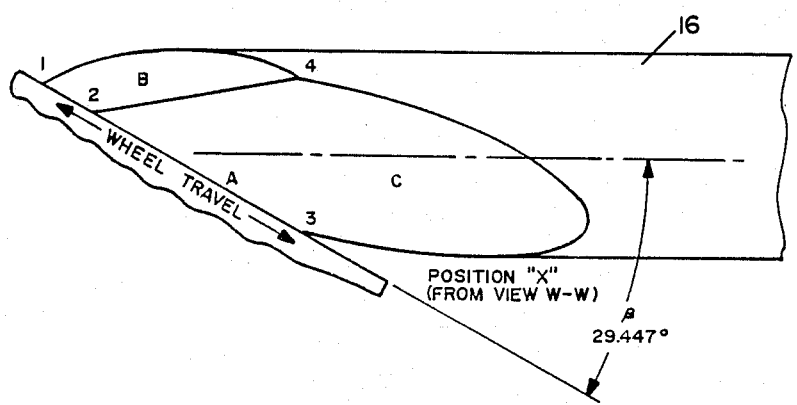
FIG. 13A illustrates the first grinding step on grinding wheel for the stylet cutting surfaces.
Figure 13B:
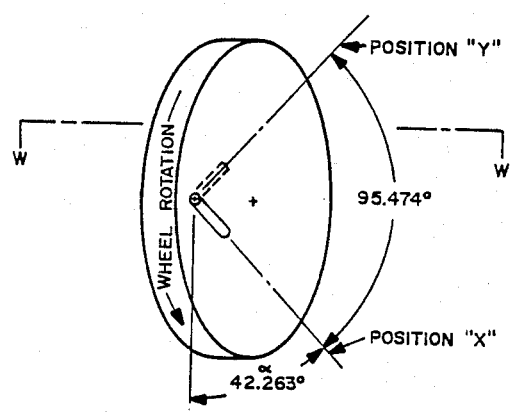
FIG. 13B illustrates the angle of approach to the grinding wheel.
Figure 13E:
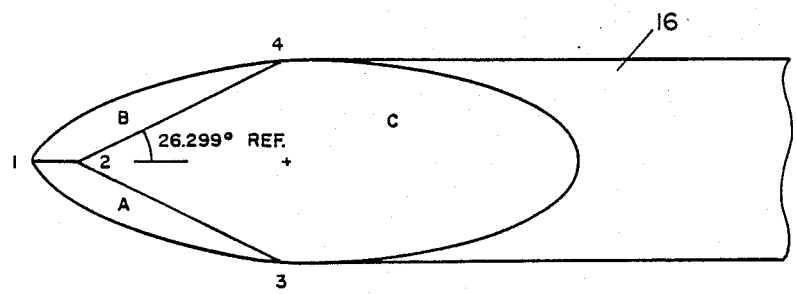
FIG. 13C and 13D illustrate the angle of rotation about the grinding wheel to grind both surfaces; and, FIG. 13E illustrates the finished style cutting surface.

FIGS. 13A-13E illustrate stylet cutting surfaces where all numerals correspond to those elements previously described. FIG. 13A illustrates positioning with respect to a grinding wheel. FIG. 13B illustrates the angle of approach to the grinding wheel. FIGS. 13C and 13D illustrate the angle of rotation to cut both cutting surfaces. FIG. 13E illustrates the finished produce.

The surface references of the tip are as follows:
Established angle $\alpha$ so that:

$$\frac{SIN\alpha(.032) + COS\alpha(.032)}{.08007} = \frac{SIN\alpha(.01914) + COS\alpha(.032)}{.06475}$$

$$\text{Then angle } \beta = TAN^{-1}\left(\frac{SIN\alpha(.032) + COS\alpha(.032)}{.08007}\right)$$

Various modifications can be made to the present invention without departing from the apparent scope thereof.

I claim:

1. A tissue needle for extraction of biopsy tissue comprising:
   a. stationary stylet means affixed in a handle and including a sharp tip;
   b. movable cannula means extending into said handle, including a configured cutting edge, for sliding coaxially over and about said stylet means;
   c. means affixing said cannular means to a linkage bar pivotally mounted in said handle;
   d. actuator trigger bar means pivotally mounted in said handle and in cam engagement with said linkage bar; and,
   e. return compression spring positioned on said cannula and between the pivoting linkage arm and the handle.

2. Tissue needle of claim 1 wherein said trigger bar means is a hand conforming grip.

3. Tissue needle of claim 1 wherein said stylet means is in a fixed relationship to said handle, and said cannula means slides co-axially over and about said stylet means including over and about a tissue sample notch at an end of said stylet means distal from said handle.

* * * * *